(12) United States Patent
de Villiers et al.

(10) Patent No.: US 7,753,956 B2
(45) Date of Patent: Jul. 13, 2010

(54) PROSTHETIC DISC FOR INTERVERTEBRAL INSERTION

(75) Inventors: Malan de Villiers, Gauteng (ZA); Ulrich Hanle, Johannesburg (ZA)

(73) Assignee: SpinalMotion, Inc., Mountain View, CA (US)

( * ) Notice: Subject to any disclaimer, the term of this patent is extended or adjusted under 35 U.S.C. 154(b) by 1362 days.

(21) Appl. No.: 10/855,253

(22) Filed: May 26, 2004

(65) Prior Publication Data

US 2005/0021145 A1 Jan. 27, 2005

Related U.S. Application Data

(60) Provisional application No. 60/473,802, filed on May 27, 2003, provisional application No. 60/473,803, filed on May 27, 2003.

(51) Int. Cl.
*A61F 2/44* (2006.01)
(52) U.S. Cl. .................................. 623/17.14
(58) Field of Classification Search .......... 606/601, 606/61; 623/17.11–17.16
See application file for complete search history.

(56) References Cited

U.S. PATENT DOCUMENTS

| | | |
|---|---|---|
| 3,486,505 A | 12/1969 | Morrison |
| 4,759,766 A | 7/1988 | Buettner-Janz et al. |
| 4,759,769 A | 7/1988 | Hedman et al. |
| 4,834,757 A | 5/1989 | Brantigan |
| 4,863,477 A | 9/1989 | Monson |
| 4,997,432 A | 3/1991 | Keller |
| 5,035,716 A | 7/1991 | Downey |
| 5,071,437 A | 12/1991 | Steffee |
| 5,122,130 A | 6/1992 | Keller |
| 5,195,526 A | 3/1993 | Michelson |
| 5,258,031 A | 11/1993 | Salib et al. |
| 5,314,477 A | 5/1994 | Marnay |
| 5,370,697 A | 12/1994 | Baumgartner |
| 5,401,269 A | 3/1995 | Buettner-Janz et al. |
| 5,415,704 A | 5/1995 | Davidson |

(Continued)

FOREIGN PATENT DOCUMENTS

DE 3023353 4/1981

(Continued)

OTHER PUBLICATIONS

Wayne G. Hellier, et al., "Wear Studies for Development of an Intervertebral Disc Prosthesis," *Spine*, (1992) vol. 17 (6), *Supplement* pp. 86-96.

(Continued)

*Primary Examiner*—Anu Ramana
(74) *Attorney, Agent, or Firm*—Townsend and Townsend and Crew LLP

(57) ABSTRACT

A prosthetic disc for insertion between adjacent vertebrae includes a core having upper and lower curved surfaces, upper and lower plates, and peripheral restraining structure on at least one of the upper plate, the lower plate and the core. Each plate has an outer surface which engages a vertebra and an inner curved surface which slides over the curved surface of the core. The peripheral restraining structure serves to hold the core against a curved surface of at least one of the plates during sliding movement of the plates over the core.

68 Claims, 3 Drawing Sheets

U.S. PATENT DOCUMENTS

| | | | |
|---|---|---|---|
| 5,507,816 | A | 4/1996 | Bullivant |
| 5,534,030 | A | 7/1996 | Navarro et al. |
| 5,556,431 | A | 9/1996 | Buttner-Janz |
| 5,674,296 | A | 10/1997 | Bryan et al. |
| 5,676,701 | A | 10/1997 | Yuan et al. |
| 5,676,702 | A | 10/1997 | Ratron |
| 5,702,450 | A | 12/1997 | Bisserie |
| 5,797,909 | A | 8/1998 | Michelson |
| 5,824,094 | A | 10/1998 | Serhan et al. |
| 5,865,846 | A | 2/1999 | Bryan et al. |
| 5,888,226 | A | 3/1999 | Rogozinski |
| 5,899,901 | A | 5/1999 | Middleton |
| 5,899,911 | A | 5/1999 | Carter |
| 5,989,291 | A | 11/1999 | Ralph et al. |
| 6,001,130 | A | 12/1999 | Bryan et al. |
| 6,019,792 | A | 2/2000 | Cauthen |
| 6,022,376 | A | 2/2000 | Assell et al. |
| 6,039,763 | A | 3/2000 | Shelokov |
| 6,096,038 | A | 8/2000 | Michelson |
| 6,139,579 | A | 10/2000 | Steffee et al. |
| 6,146,421 | A * | 11/2000 | Gordon et al. ............ 623/17.15 |
| 6,156,067 | A | 12/2000 | Bryan et al. |
| 6,162,252 | A | 12/2000 | Kuras et al. |
| 6,235,030 | B1 | 5/2001 | Zuckerman et al. |
| 6,261,296 | B1 | 7/2001 | Aebi et al. |
| 6,290,726 | B1 * | 9/2001 | Pope et al. ................ 623/22.15 |
| 6,315,797 | B1 | 11/2001 | Middleton |
| 6,348,071 | B1 | 2/2002 | Steffee et al. |
| 6,368,350 | B1 | 4/2002 | Erickson et al. |
| 6,416,551 | B1 | 7/2002 | Keller |
| 6,447,544 | B1 | 9/2002 | Michelson |
| 6,478,800 | B1 | 11/2002 | Fraser et al. |
| 6,517,580 | B1 * | 2/2003 | Ramadan et al. ......... 623/17.15 |
| 6,520,996 | B1 * | 2/2003 | Manasas et al. ............ 623/23.5 |
| 6,527,804 | B1 * | 3/2003 | Gauchet et al. .......... 623/17.12 |
| 6,562,047 | B2 | 5/2003 | Ralph et al. |
| 6,582,466 | B1 * | 6/2003 | Gauchet .................... 623/17.11 |
| 6,592,624 | B1 | 7/2003 | Fraser et al. |
| 6,599,294 | B2 | 7/2003 | Fuss et al. |
| 6,607,558 | B2 | 8/2003 | Kuras |
| 6,610,092 | B2 | 8/2003 | Ralph et al. |
| 6,645,248 | B2 | 11/2003 | Casutt |
| 6,652,533 | B2 | 11/2003 | O'Neil |
| 6,666,866 | B2 | 12/2003 | Martz et al. |
| 6,669,732 | B2 * | 12/2003 | Serhan et al. ............ 623/17.16 |
| 6,682,562 | B2 * | 1/2004 | Viart et al. ................ 623/17.14 |
| 6,689,132 | B2 | 2/2004 | Biscup |
| 6,706,068 | B2 | 3/2004 | Ferree |
| 6,712,825 | B2 | 3/2004 | Aebi et al. |
| 6,726,720 | B2 | 4/2004 | Ross et al. |
| 6,740,118 | B2 | 5/2004 | Eisermann et al. |
| 6,770,095 | B2 | 8/2004 | Grinberg et al. |
| 6,814,737 | B2 | 11/2004 | Cauthen |
| 6,875,213 | B2 | 4/2005 | Michelson |
| 6,963,071 | B2 | 11/2005 | Bristol |
| 6,964,686 | B2 * | 11/2005 | Gordon .................... 623/17.14 |
| 6,966,929 | B2 | 11/2005 | Mitchell |
| 6,994,727 | B2 * | 2/2006 | Khandkar et al. ........ 623/17.15 |
| 7,025,787 | B2 | 4/2006 | Bryan et al. |
| 7,179,294 | B2 * | 2/2007 | Eisermann et al. ....... 623/17.15 |
| 2001/0016773 | A1 | 8/2001 | Serhan et al. |
| 2001/0029377 | A1 | 10/2001 | Aebi et al. |
| 2001/0056302 | A1 * | 12/2001 | Boyer et al. ............. 623/17.15 |
| 2002/0035400 | A1 | 3/2002 | Bryan et al. |
| 2002/0045904 | A1 | 4/2002 | Fuss et al. |
| 2002/0128715 | A1 | 9/2002 | Bryan et al. |
| 2002/0198532 | A1 | 12/2002 | Michelson |
| 2003/0009224 | A1 | 1/2003 | Kuras |
| 2003/0040746 | A1 * | 2/2003 | Mitchell et al. ............... 606/61 |
| 2003/0074076 | A1 | 4/2003 | Ferree et al. |
| 2003/0100951 | A1 | 5/2003 | Serhan et al. |
| 2003/0135277 | A1 | 7/2003 | Bryan et al. |
| 2003/0191536 | A1 | 10/2003 | Ferree |
| 2003/0199982 | A1 | 10/2003 | Bryan |
| 2003/0204261 | A1 | 10/2003 | Eisermann et al. |
| 2003/0208271 | A1 | 11/2003 | Kuras |
| 2004/0002761 | A1 * | 1/2004 | Rogers et al. ............ 623/17.13 |
| 2004/0024407 | A1 | 2/2004 | Ralph |
| 2004/0030391 | A1 | 2/2004 | Ferree |
| 2004/0073312 | A1 | 4/2004 | Eisermann et al. |
| 2004/0143270 | A1 | 7/2004 | Zucherman et al. |
| 2004/0176843 | A1 | 9/2004 | Zubok et al. |
| 2005/0021145 | A1 | 1/2005 | de Villiers et al. |
| 2005/0021146 | A1 | 1/2005 | de Villiers et al. |
| 2005/0043800 | A1 | 2/2005 | Paul et al. |
| 2005/0085917 | A1 | 4/2005 | Marmay et al. |
| 2005/0107881 | A1 | 5/2005 | Alleyne et al. |
| 2005/0149189 | A1 | 7/2005 | Mokhtar et al. |
| 2005/0192586 | A1 | 9/2005 | Zuckerman et al. |
| 2005/0192670 | A1 | 9/2005 | Zubok et al. |
| 2005/0197706 | A1 | 9/2005 | Hovorka et al. |
| 2005/0251262 | A1 | 11/2005 | de Villiers et al. |
| 2005/0261772 | A1 | 11/2005 | Filippi et al. |
| 2006/0004453 | A1 | 1/2006 | Bartish et al. |
| 2006/0025862 | A1 | 2/2006 | de Villiers et al. |
| 2006/0036325 | A1 | 2/2006 | Paul et al. |
| 2006/0041313 | A1 | 2/2006 | Allard et al. |
| 2006/0293754 | A1 | 12/2006 | de Villiers et al. |
| 2007/0061011 | A1 | 3/2007 | de Villiers et al. |

FOREIGN PATENT DOCUMENTS

| | | | |
|---|---|---|---|
| EP | 0333990 | A2 | 9/1989 |
| EP | 0560140 | A1 | 9/1993 |
| EP | 0560141 | A1 | 9/1993 |
| EP | 591712 | A1 | 4/1994 |
| EP | 1142544 | A1 | 10/2001 |
| EP | 1153582 | A2 | 11/2001 |
| EP | 1250898 | A1 | 10/2002 |
| EP | 1306064 | A1 | 5/2003 |
| EP | 1344493 | A1 | 9/2003 |
| EP | 1344506 | A1 | 9/2003 |
| EP | 1344507 | A1 | 9/2003 |
| EP | 1344508 | A1 | 9/2003 |
| EP | 1417940 | A1 | 5/2004 |
| JP | 63-164948 | | 7/1988 |
| WO | WO 00/35384 | * | 6/2000 |
| WO | WO 01/01893 | A1 | 1/2001 |
| WO | WO 2004/026187 | A1 | 4/2004 |
| WO | WO 2005/053580 | A1 | 6/2005 |
| ZA | 03/9312 | | 11/2003 |

OTHER PUBLICATIONS

Karin Butttner-Janz, "The Development pf the Artifical Disc," Introduction, (1989) pp. 1-18, Library of Congress Catalogue No. 92-75582, ISBN 0-9635430-0-8.

International Search Report PCT/US05/26160 Jul. 21, 2005.

J.C. Le Huec et al., "Shock Absorption in Lumber Disc Prosthesis," *Journal of Spinal Disorders & Techniques*, vol. 16, No. 4, pp. 346-351.

Choon-Ki Lee, MD, et al., "Impact Response of the Intervertebral Disc in a Finite-Element Model," *Spine* vol. 25, No. 19, pp. 2431-2439.

Japanese Office Action of Patent Application No. 2006-533469, dated Jun. 22, 2009, [English Translation Included], 8 pages total.

* cited by examiner

PROSTHETIC DISC FOR INTERVERTEBRAL INSERTION

CROSS-REFERENCES TO RELATED APPLICATIONS

This application claims the priority of U.S. Provisional Patent Application Ser. Nos. 60/473,802, entitled "Prosthetic Disc for Intervertebral Insertion," and 60/473,803, entitled "Intervertebral Prosthetic Disc," both of which were filed May 27, 2003, the full disclosures of which are hereby incorporated by reference.

BACKGROUND OF THE INVENTION

1. Field of the Invention

This invention relates to medical devices and methods. More specifically, the invention relates to a prosthetic disc for intervertebral insertion, such as in the lumbar and cervical spine.

In the event of damage to a lumbar or cervical intervertebral disc, one possible surgical treatment is to replace the damaged disc with a disc prosthesis. Several types of intervertebral disc prostheses are currently available. For example, one type of intervertebral disc prosthesis is provided by Waldemar Link GmbH & Co under the trademark LINK® SB Charite. This prosthesis includes upper and lower prosthesis plates or shells which locate against and engage the adjacent vertebral bodies, and a low friction core between the plates. The core has upper and lower convexly curved surfaces and the plates have corresponding, concavely curved recesses which cooperate with the curved surfaces of the core. This allows the plates to slide over the core to allow required spinal movements to take place. The curved recesses in the plates are surrounded by annular ridges which locate, at the limit of sliding movement of the plates over the core, in opposing upwardly and downwardly facing, peripheral channels surrounding the curved surfaces of the core.

This type of disc configuration is described in EP 1142544A1 and EP 1250898A1, assigned to Waldemar Link GmbH & Co. A drawback of such configurations is that the provision of the peripheral ribs and channels limits the areas available for bearing and sliding contact between the plates and core, and accordingly the loads which can be transmitted by the prosthesis. As a result of the relatively small bearing areas, it is believed that at least the core will be subject to rapid wear and have a relatively short lifespan. Also, because the core is in effect merely "clamped" between the plates, this configuration does not allow for secure retention of the core. In one alternative arrangement, the curved surfaces of the core carry opposing, elongate keys that locate in elongate grooves in the plates and another alternative arrangement in which the plates have opposing elongate keys that locate in elongate grooves in the opposite curved surfaces of the core. These key and groove arrangements allow the plates to slide over the core within the limits of the length of the grooves, in one direction only. Although allowance is made for some lateral play of the keys in the grooves, very little sliding movement of the plates over the core can take place in the orthogonal vertical plane, and this is considered to be a serious drawback of this design.

Other currently available intervertebral disc prostheses have similar and/or other drawbacks. Typically, drawbacks include insufficient resistance to wear and tear, restricted range of motion and/or insufficient ability of the prosthesis to adhere to vertebral bone.

Therefore, a need exists for improved intervertebral disc prostheses. Ideally, such improved prostheses would resist wear and tear, provide a desired range of motion and adhere well to vertebral bone. At least some of these objectives will be met by the present invention.

2. Description of the Background Art

Published U.S. patent applications Nos. 2002/0035400A1 and 2002/0128715A1 describe disc implants which comprise opposing plates with a core between them over which the plates can slide. The core receives one or more central posts, which are carried by the plates and which locate in opposite ends of a central opening in the core. Such arrangements limit the load bearing area available between the plates and core.

Other patents related to intervertebral disc prostheses include U.S. Pat. Nos. 4,759,766; 4,863,477; 4,997,432; 5,035,716; 5,071,437; 5,370,697; 5,401,269; 5,507,816; 5,534,030; 5,556,431; 5,674,296; 5,676,702; 5,702,450; 5,824,094; 5,865,846; 5,989,291; 6,001,130; 6,022,376; 6,039,763; 6,139,579; 6,156,067; 6,162,252; 6,315,797; 6,348,071; 6,368,350; 6,416,551; 6,592,624; 6,607,558 and 6,706,068. Other patent applications related to intervertebral disc prostheses include U.S. Patent Application Publication Nos.: 2003/0009224; 2003/0074076; 2003/0191536; 2003/0208271; 2003/0135277; 2003/0199982; 2001/0016773 and 2003/0100951. Other related patents include WO 01/01893A1, EP 1344507, EP 1344506, EP 1250898, EP 1306064, EP 1344508, EP 1344493, EP 1417940, EP 1142544, and EP 0333990.

BRIEF SUMMARY OF THE INVENTION

In one aspect of the present invention, a prosthetic disc for insertion between adjacent vertebrae includes upper and lower plates having outer surfaces, which engage and are locatable against the respective vertebrae, and inner curved surfaces. A core is disposed between the curved surfaces to allow the plates to slide over the core. Preferably, the plates can slide freely in all directions, not being limited to movement in a single direction as with the prior art. The present invention further provides peripheral restraining structure on one or both of the plates or the core to hold the core against the curved surface of at least one of the plates during sliding movement of the plates over the core. The peripheral restraining structure defines a limit or boundary for movement of the core relative to at least one of the upper and lower plates. Within such a peripheral boundary, however, movement of the core relative to the plate will preferably be unconstrained. That is, movement of the core relative to the plate may occur in any direction without significant inhibition or friction. The core will preferably not be attached to either the upper or lower plate, and the plates will thus be able to freely articulate relative to each other over the core, which provides a low friction bearing surface.

An advantage of the structure thus described is that the surface contact area between the core and each of the upper and lower plates may be maximized. By providing only a peripheral restraint, as opposed for example to grooves and keys on the surface of the core and plates, the width or diameter of the core relative to the size of the plate may be maximized. Moreover, the surfaces of the core and the plates which contact each other may be made smooth and free from other structure(s) that might adversely affect performance. In the preferred embodiments, both the curved surfaces of the plates and the corresponding surfaces of the core will be spherical sections. The use of spherical surfaces promotes free, unconstrained relative motion of the plates and the core in all directions.

In some embodiments, the peripheral restraining structure limits relative inclination of the plates during sliding movement of the plates over the core, usually by defining a stop structure. In other embodiments, the peripheral restraining structure lifts one side of the core relative to an opposite side of the core during sliding movement of the plates over the core. The peripheral restraining structure itself may take any of a number of different forms. In one embodiment, for example, the restraining structure comprises a ring structure on at least one of the upper and lower plates and an annular structure on at least a portion of the periphery of the core. The ring structure will be adapted to engage and restrain the annular structure on the core. For example, the ring structure may comprise a flange which defines an overhang over at least a portion of the periphery of one of the plates. The overhang of the flange will receive the annular structure on the core to provide an interference fit which retains the core against the curved surface of the plate but allows the core to slide freely and in an unconstrained manner within the limit or boundary defined by the flange. The annular structure on the core may be a rim which extends continuously or discontinuously (preferably continuously) around a lateral circumference of the core. By providing a rim which has a width, usually a diameter, which is slightly greater than the corresponding width of an inner edge of the flange at one point, the core will be held in place and will not be dislodged from the cavity defined by the ring structure in normal use.

Usually, the flange or other ring structure as well as the rim or other annular structure will be formed continuously about the periphery of the plate and core, respectively. Alternatively, however, either or both of the annular structure and the ring structure could be formed discontinuously. That is, so long as at least some portion of the ring structure and the annular structure remain engaged during all expected geometries and uses of the prosthetic disc, the objective of holding the core against the curved surface of the plate will be met.

The upper and lower plates may be made of any suitable material or combination of materials, such as but not limited to cobalt chrome molybdenum and titanium. In some embodiments, titanium plates are used, and these plates may optionally include inner surfaces of titanium nitride and outer surfaces that are aluminum oxide blasted to create micro-concavities. In another embodiment, cobalt chrome plates are used, with the outer surfaces being blasted with aluminum oxide and then coated with a titanium plasma spray. In some embodiments, the plates comprise an MRI-compatible material, such as titanium, coupled with a hardened material, such as cobalt chrome molybdenum. Such materials may be coupled using any suitable means, such as laminating, slip fitting, interferences fitting, adhesion, welding, molding or the like. Some plates include a coating or material on the inner surfaces for reducing friction and/or wear and tear, such as a titanium nitride surface.

Optionally, in some embodiments the outer surfaces of the upper and lower plates have at least one surface feature for promoting attachment of the outer surfaces to the vertebrae. For example, such surface features may include a plurality of serrations disposed along the outer surfaces. Some embodiments include additional or alternative features on the outer surfaces for enhancing attachment of the prosthesis to vertebral bone, such as a material or coating, like a titanium plasma spray. Multiple micro-concavities may be formed on the outer surfaces, for example by aluminum oxide spraying, to further enhance attachment. Additionally or alternatively, the surface features may include at least one fin disposed on each of the outer surfaces. In some embodiments, the fin includes at least one hole for further promoting attachment to the vertebrae. Fins may extend vertically from their corresponding outer surfaces at right angles, or alternatively the fins may extend from their corresponding outer surface at angles other than 90°. Fins may also have any suitable orientation relative to the anterior-posterior axis of the prosthesis. For example, a fin may extend in a straight line from anterior to posterior, without being angled. Alternatively, the fin may be rotated or angled away from the anterior-posterior axis at any suitable angle between 0° and 180°. In one embodiment, each fin is disposed in a lateral orientation on the outer surfaces.

The core may generally have any suitable configuration and be made of any suitable material or combination of materials, such as polymers, ceramics or the like. In some embodiments, the core comprises a low-friction material and has two convex surfaces for slidably engaging the inner, curved surfaces of the upper and lower plates.

In another aspect of the present invention, a prosthetic disc for insertion between adjacent vertebrae includes upper and lower plates and a free-floating core disposed between the plates. Again, the upper and lower plates have outer surfaces locatable against the respective vertebrae and inner, curved surfaces. Additionally, at least one of the upper and lower plates includes a flange extending from one of the inner surfaces. The core includes at least one peripheral groove for engaging with the flange(s) to hold the core captive between the plates during sliding movement of the plates over the core. Any of the features described above may also be incorporated in various embodiments.

In another aspect of the present invention, a prosthetic disc for insertion between adjacent vertebrae includes upper and lower plates having outer surfaces locatable against the respective vertebrae and inner, curved surfaces, at least one of the upper and lower plates including a flange extending from one of the inner surfaces. A free-floating core is disposed between the curved surfaces to allow the plates to slide over the core, and the core includes at least one peripheral protrusion for engaging with the flange(s) to hold the core captive between the plates during sliding movement of the plates over the core. Again, various embodiments may include any of the features described above.

In yet another aspect of the invention, a prosthetic disc for insertion between adjacent vertebrae includes upper and lower plates having outer surfaces locatable against the respective vertebrae and inner curved surfaces, a core between the plates, and opposing retaining formations. The core includes upper and lower curved surfaces complementary in shape to the inner, curved surfaces of the plates to allow the plates to slide over the core, the upper and lower surfaces of the core being located respectively above and below an equatorial plane extending laterally through the core. The opposing retaining formations are located peripherally on the equatorial plane of the core and at an edge of the curved surface of at least one of the plates and serve to hold the core captive between the plates during sliding movement of the plates over the core.

In yet another aspect of the invention, a method for restraining spacing between adjacent vertebrae involves implanting an upper plate against a lower surface of an upper vertebral body, implanting a lower plate against an upper surface of a lower vertebral body, and disposing a core between the upper and lower plates The core floats between spherical cavities in each of the upper and lower plates, the plates restraining peripheral movement of the core using at least one peripheral restraining member. In some embodiments, implanting each of the plates comprises sliding a fin on each plate into a corresponding groove formed in its respective vertebral body. The fin may slide into the groove in any suitable direction, such as posterior-anterior, anterior-posterior, lateral, or any angled direction between an anterior-posterior orientation and a lateral orientation. Optionally, implanting may further involve contacting textured outer surfaces of the upper and lower plates with the upper and lower surfaces of the vertebral bodies.

In another aspect of the invention, a method for assembling a prosthetic disc for insertion between adjacent vertebrae involves movably coupling a core with a first endplate to form an interference fit between the core and the first endplate and contacting the core with a second endplate. In some embodiments, coupling the core with the first endplate comprises snap fitting the core into the endplate. Alternatively, coupling the core with the first endplate may comprise forming the endplate around the core. In some embodiments, coupling the core with the first endplate involves engaging a peripheral protrusion of the core with a peripheral restraining structure of the first endplate.

These and other aspects and embodiments will be described in further detail below, with reference to the drawing figures.

DETAILED DESCRIPTION OF THE INVENTION

Figure 1:
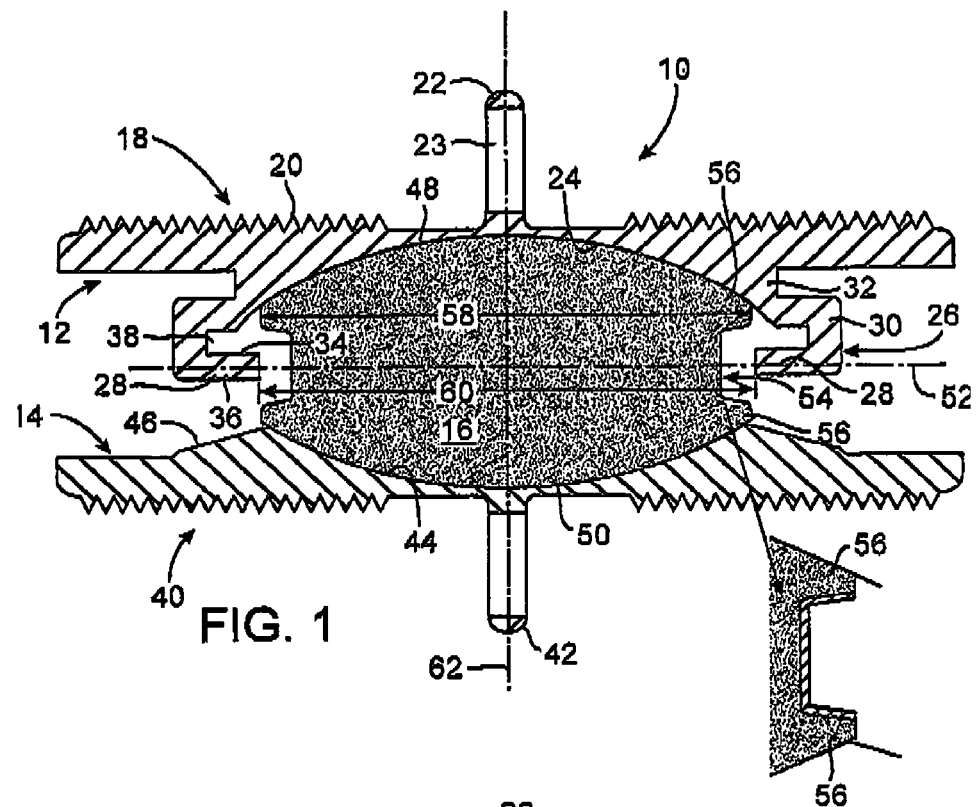
FIG. 1 shows a cross-sectional anterior view of a prosthetic disc with the prosthesis plates and core in vertical alignment, according to one embodiment of the present invention.

FIGS. 1 to 4 illustrate a prosthetic disc 10 for intervertebral insertion between two adjacent spinal vertebrae (not shown). The disc 10 comprises three components, namely an upper plate or shell 12, a lower plate or shell 14 and a core 16 located between the plates.

The upper plate 12 includes an outer surface 18 and an inner surface 24 and may be constructed from any suitable material or combination of materials, such as but not limited to cobalt chrome molybdenum, titanium (such as grade 5 titanium) and/or the like. In one embodiment, typically used in the lumbar spine, the upper plate 12 is constructed of cobalt chrome molybdenum, and the outer surface 18 is treated with aluminum oxide blasting followed by a titanium plasma spray. In another embodiment, typically used in the cervical spine, the upper plate 12 is constructed of titanium, the inner surface 24 is coated with titanium nitride, and the outer surface 18 is treated with aluminum oxide blasting. An alternative cervical spine embodiment includes no coating on the inner surface 24. In some embodiments, it may be useful to couple two materials together to form the inner surface 24 and the outer surface 18. For example, the upper plate 12 may be made of an MRI-compatible material, such as titanium, but may include a harder material, such as cobalt chrome molybdenum, for the inner surface 24. Any suitable technique may be used to couple materials together, such as snap fitting, slip fitting, lamination, interference fitting, use of adhesives, welding and/or the like. Any other suitable combination of materials and coatings may be employed in various embodiments of the invention.

Figure 6:
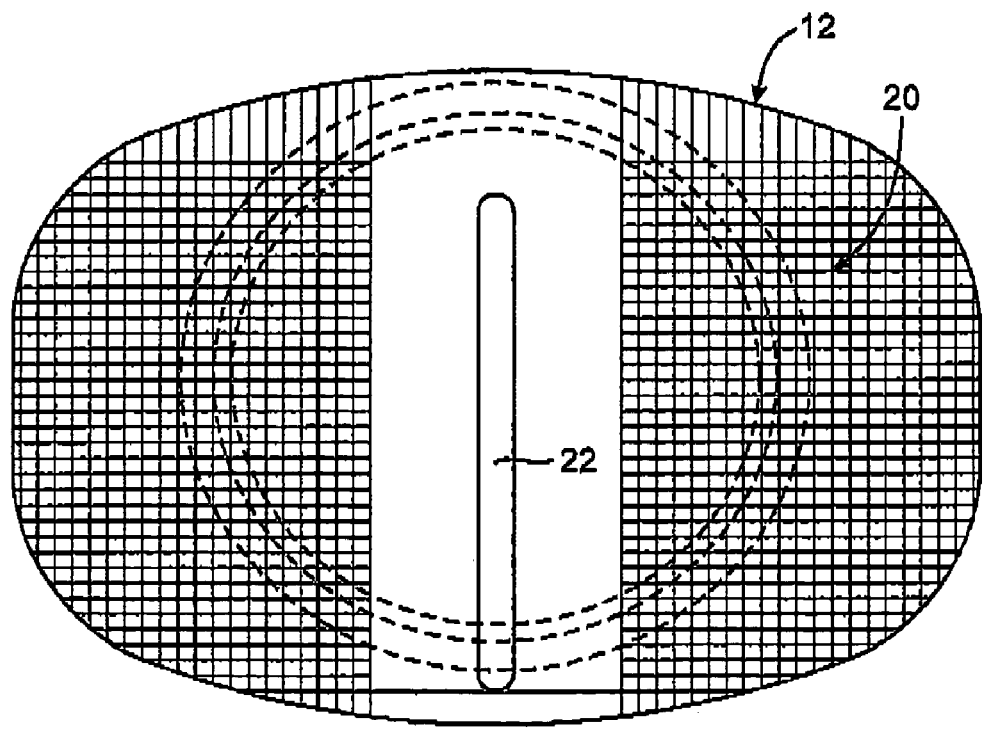
FIG. 6 shows a plan view of an upper plate of a prosthetic disc, according to one embodiment of the present invention.

In some embodiments, the outer surface 18 is planar. Oftentimes, the outer surface 18 will include one or more surface features and/or materials to enhance attachment of the prosthesis 10 to vertebral bone. For example, the outer surface 18 may be machined to have a serrations 20 or other surface features for promoting adhesion of the upper plate 12 to a vertebra. In the embodiment shown (FIG. 6), the serrations 20 extend in mutually orthogonal directions, but other geometries would also be useful. Additionally, the outer surface 18 may be provided with a rough microfinish formed by blasting with aluminum oxide microparticles or the like. In some embodiments, the outer surface may also be titanium plasma sprayed to further enhance attachment of the outer surface 18 to vertebral bone.

The outer surface 18 may also carry an upstanding, vertical fin 22 extending in an anterior-posterior direction. The fin 22 is pierced by transverse holes 23. In alternative embodiments, the fin 22 may be rotated away from the anterior-posterior axis, such as in a lateral-lateral orientation, a posterolateral-anterolateral orientation, or the like. In some embodiments, the fin 22 may extend from the surface 18 at an angle other than 90°. Furthermore, multiple fins 22 may be attached to the surface 18 and/or the fin 22 may have any other suitable configuration, in various embodiments. In other embodiments, the fin 22 In some embodiments, such as discs 10 for cervical insertion, the fins 22, 42 may be omitted altogether.

The inner, spherically curved concave surface 24 is formed at a central, axial position with a circular recess 26 as illustrated. At the outer edge of the curved surface 24, the upper plate 12 carries peripheral restraining structure comprising an integral ring structure 26 including an inwardly directed rib or flange 28. The flange 28 forms part of a U-shaped member 30 joined to the major part of the plate by an annular web 32. The flange 28 has an inwardly tapering shape and defines upper and lower surfaces 34 and 36 respectively which are inclined slightly relative to the horizontal when the upper plate 12 is at the orientation seen in FIG. 1. An overhang 38 of the U-shaped member 30 has a vertical dimension that tapers inwardly as illustrated.

The lower plate 14 is similar to the upper plate 12 except for the absence of the peripheral restraining structure 26. Thus, the lower plate 14 has an outer surface 40 which is planar, serrated and microfinished like the outer surface 18 of the upper plate 12. The lower plate 14 optionally carries a fin 42 similar to the fin 22 of the upper plate. The inner surface 44 of the lower plate 14 is concavely, spherically curved with a radius of curvature matching that of the inner surface 24 of the upper plate 12. Once again, this surface may be provided with a titanium nitride or other finish.

At the outer edge of the inner curved surface 44, the lower plate 14 is provided with an inclined ledge formation 46. Alternatively, the lower plate 14 may include peripheral restraining structure analogous to the peripheral restraining structure 26 on the upper plate 12.

The core 16 of the disc 10 is made of a low-friction material, such as polyethylene (Chirulen™). In alternative embodiments, the core 16 may comprise any other suitable material, such as other polymers, ceramics or the like. The core 16 has identical upper and lower spherically curved convex surfaces 48, 50. The radius of curvature of these surfaces matches the radius of curvature of the inner surfaces 24, 44 of the upper and lower plates 12, 14. The curved surfaces are accordingly complementary. For wear resistance, the surface zones of the core may be hardened by an appropriate cross-linking procedure.

The core 16 is symmetrical about a central, equatorial plane 52 which bisects it laterally. (Although in other embodiments, the core 16 may be asymmetrical.) Lying on this equatorial plane is an annular recess or groove 54 which extends about the periphery of the core. The groove 54 is defined between upper and lower ribs or lips 56. When the plates 12, 14 and core 16 are assembled and in the orientation seen in FIG. 1, the flange 28 lies on the equatorial plane and directly aligned with the groove 54. The outer diameter 58 of the lips 56 is preferably very slightly larger than the diameter 60 defined by the inner edge of the flange 28. Assembly of the core and upper plate may involve pressing the core through the circular aperture defined by the flange 28, with the inherent resilience of the core allowing the minor deformation of the upper rib 56, or that the core be introduced at an inclination. In other less preferred embodiments of the invention (not shown), the diameter 58 may be equal to or even slightly less than the diameter 60.

In some embodiments, the inner surface of the groove 54 may be provided, for wear resistance, with a lining of pure titanium or titanium impregnated with cobalt chrome, titanium nitride, other titanium alloy or the like.

Figure 4:
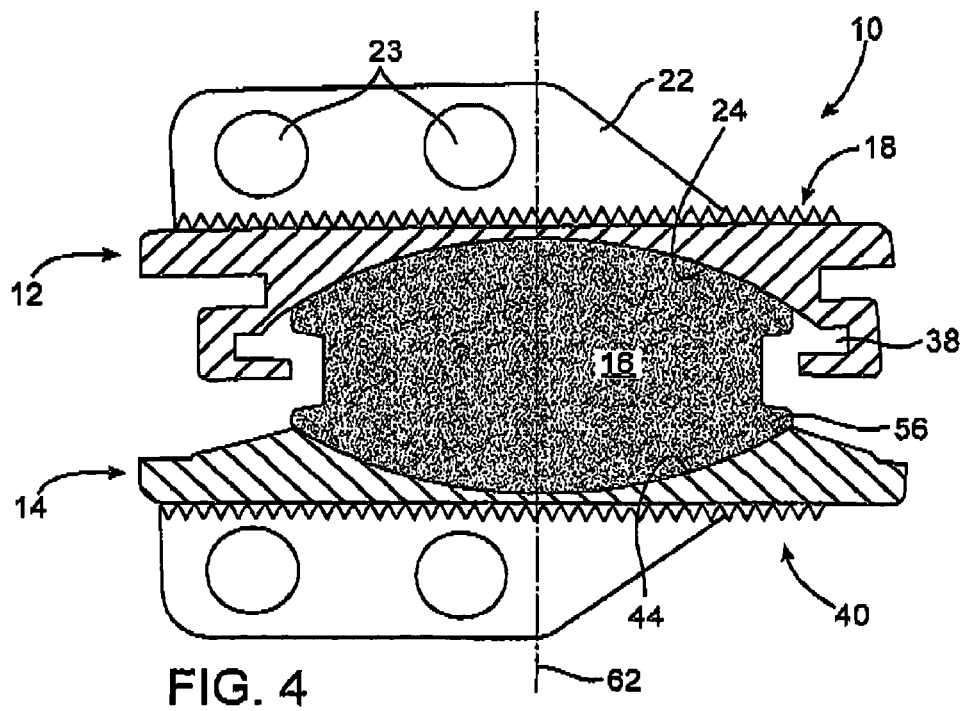
FIG. 4 shows a side view of the prosthetic disc in FIG. 1 with the prosthesis plates and core in vertical alignment.

The central axis of the disc 10 (the axis passing through the centers of curvature of the curved surfaces) is indicated with the reference numeral 62. As shown in FIG. 1, the disc 10 may be symmetrical about a central anterior-posterior plane containing the axis 62. Referring to FIG. 4, in some embodiments the axis 62 is posteriorly disposed, i.e. is located closer to the posterior limit of the disc than the anterior limit thereof.

In use, the disc 10 is surgically implanted between adjacent spinal vertebrae in place of a damaged disc. The adjacent vertebrae are forcibly separated from one another to provide the necessary space for insertion. The disc is inserted, normally in a posterior direction, into place between the vertebrae with the fins 22, 42 of the plates 12, 14 entering slots cut in the opposing vertebral surfaces to receive them. After insertion, the vertebrae, facets, adjacent ligaments and soft tissues are allowed to move together to hold the disc in place. The serrated and microfinished surfaces 18, 40 of the plates 12, 14 locate against the opposing vertebrae. The serrations 20 and fins 22, 42 provide initial stability and fixation for the disc 10. With passage of time, enhanced by the titanium surface coating, firm connection between the plates and the vertebrae will be achieved as bone tissue grows over the serrated surface. Bone tissue growth will also take place about the fins 22, 40 and through the transverse holes 23 therein, further enhancing the connection which is achieved.

Figure 5:
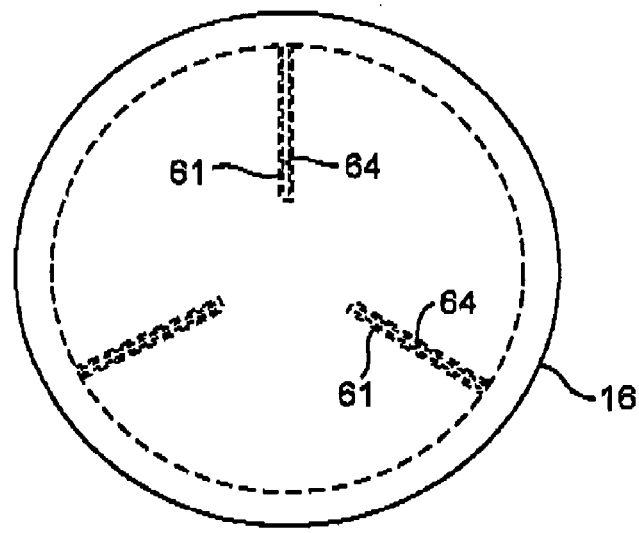
FIG. 5 shows a plan view of a core of a prosthetic disc, according to one embodiment of the present invention.

Referring to FIG. 5, the core 16 may be formed with narrow, angularly spaced, blind passages 61 which accommodate titanium pins 64. In many embodiments, the core 16 itself is transparent to X-radiation and so is invisible in a post-operative X-ray examination. The pins 64 serve as radiographic markers and enable the position of the core 16 to be ascertained during such examination.

Figure 2:
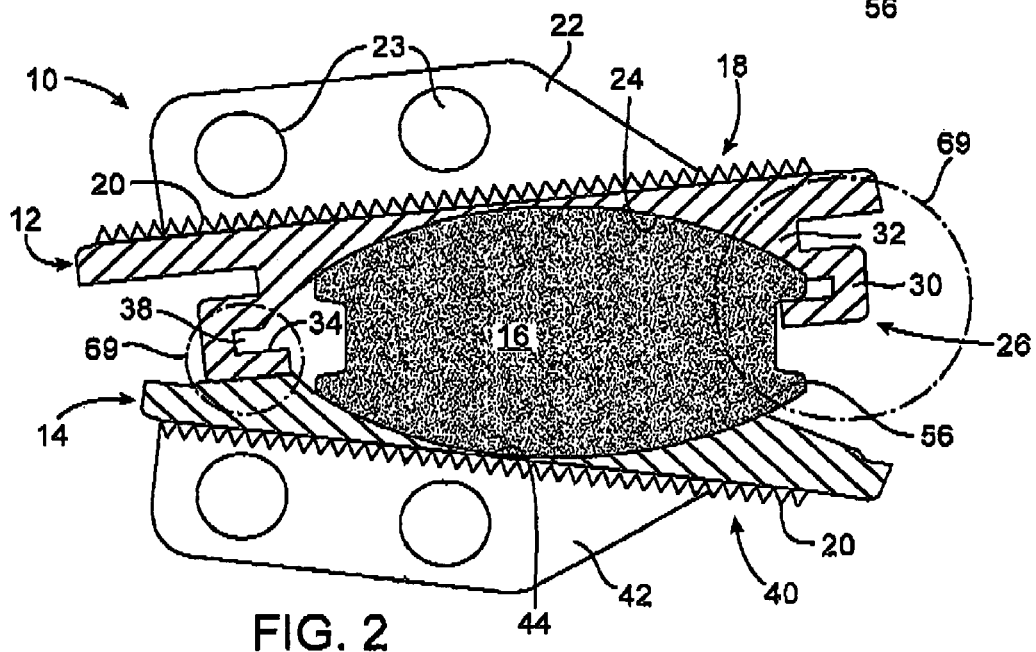
FIG. 2 shows a side view of the prosthetic disc in FIG. 1 after sliding movement of the plates over the core.

In the assembled disc 10, the complementary and cooperating spherical surfaces of the plates and core allow the plates to slide or articulate over the core through a fairly large range of angles and in all directions or degrees of freedom, including rotation about the central axis 62. FIGS. 1 and 4 show the disc 10 with the plates 12 and 14 and core 16 aligned vertically with one another on the axis 62. FIG. 2 illustrates a situation where maximum anterior flexion of the disc 10 has taken place. At this position, the upper rib 56 has entered the hollow 38 of the U-shaped member 30, the lower surface of the rib 56 has moved into contact with the upper surface 34 of the flange 28, the flange having moved into the groove 54, and the lower surface 36 of the flange has moved into contact with the upper surface of the ledge formation 46, as will be seen in the encircled areas 69. Abutment between the various surfaces prevents further anterior flexure. The design also allows for the inner extremity of the flange 28 to abut against the base of the groove 54, thereby limiting further relative movement between the core and plate. A similar configuration is achieved in the event of maximum posterior flexure of the plates 12, 14 over the core, such as during spinal extension and/or in the event of maximum lateral flexure.

Figure 3:
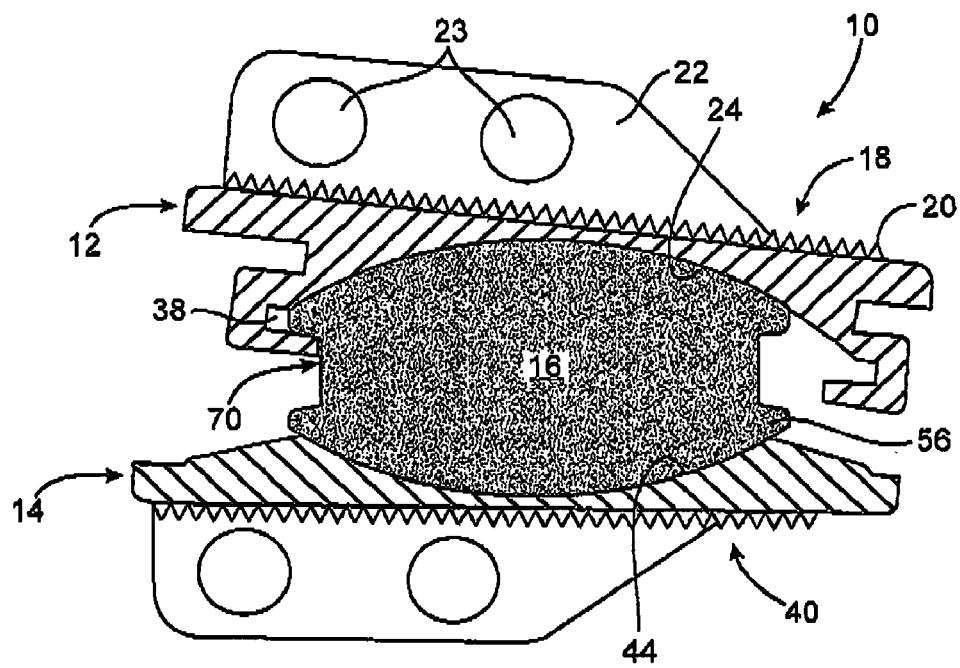
FIG. 3 shows a side view of the prosthetic disc in FIG. 1 after translational movement of the plates relative to the core.

FIG. 3 illustrates how the disc 10 can also allow for translational movement of the plates relative to the core. In the illustrated situation there has been lateral translation of the plates relative to the core. The limit of lateral translation is reached when the inner extremity of the flange 28 abuts the base of the groove 54 as indicated by the numeral 70.

The flange 28 and the groove 54 defined between the ribs 56, prevent separation of the core from the plates. In other words, the cooperation of the retaining formations ensures that the core is held captive between the plates at all times during flexure of the disc 10.

In an alternative embodiment, the continuous annular flange 28 may be replaced by a retaining formation comprising a number of flange segments which are spaced apart circumferentially. Such an embodiment could include a single, continuous groove 54 as in the illustrated embodiment. Alternatively, a corresponding number of groove-like recesses spaced apart around the periphery of the core could be used, with each flange segment opposing one of the recesses. In another embodiment, the continuous flange or the plurality of flange segments could be replaced by inwardly directed pegs or pins carried by the upper plate 12. This embodiment could include a single, continuous groove 54 or a series of circumferentially spaced recesses with each pin or peg opposing a recess.

In yet another embodiment, the retaining formation(s) could be carried by the lower plate 14 instead of the upper plate, i.e. the plates are reversed. In some embodiments, the upper (or lower) plate is formed with an inwardly facing groove, or circumferentially spaced groove segments, at the edge of its inner, curved surface, and the outer periphery of the core is formed with an outwardly facing flange or with circumferentially spaced flange segments.

Although the foregoing is a complete and accurate description of the invention, any of a number of modifications, additions or the like may be made to the various embodiments without departing from the scope of the invention. Therefore, nothing described above should be interpreted as limiting the scope of the invention at it is described in the claims.

What is claimed is:

1. A prosthetic disc for insertion between adjacent vertebrae, the prosthetic disc comprising:
    a mobile core having upper and lower curved surfaces;
    upper and lower plates, each plate having an outer surface which engages a vertebra and an inner curved surface which slides and translates over the curved surface of the mobile core when the prosthetic disc is implanted, wherein the upper and lower curved surfaces of the core comprise two oppositely facing convex low-friction surfaces which slidably engage the inner curved surfaces of the upper and lower plates; and
    a peripheral restraining structure on at least one of the upper plate, the lower plate and the core, the peripheral restraining structure configured to hold the mobile core against a curved surface of at least one of the plates during sliding movement of the plates over the core, wherein the peripheral restraining structure is located on at least one of the plates and contacts the other plate to limit relative inclination of the plates during sliding movement of the plates over the core, wherein the other plate comprises a formation that contacts the peripheral restraining structure to limit relative inclination of the plates during sliding movement of the plates over the core.

2. A prosthetic disc as in claim 1, wherein at least one of the curved surfaces is spherical.

3. A prosthetic disc as in claim 2, wherein both curved surfaces are spherical.

4. A prosthetic disc as in claim 1, wherein movement of the core within the peripheral restraining structure is unconstrained.

5. A prosthetic disc as in claim 1, wherein the peripheral restraining structure defines a stop structure to limit relative inclination of the plates during sliding movement of the plates over the core.

6. A prosthetic disc as in claim 1, wherein the peripheral restraining structure will engage one side of the core to lift an opposite side of the core during sliding movement of the plates over the core.

7. A prosthetic disc as in claim 1, wherein the peripheral restraining structure comprises:
an annular structure extending over at least a portion of the periphery of the core; and
a ring structure on one of the upper and lower plates, which ring structure engages and retains the annular structure.

8. A prosthetic disc as in claim 7, wherein the ring structure comprises a flange which defines an overhang, and wherein at least part of the annular structure on the core extends into the overhang to provide an interference fit of the core with the flange.

9. A prosthetic disc as in claim 8, wherein the annular structure comprises a rim which extends continuously around a lateral circumference of the core, the rim having a greater width at least some locations than a width of an inner edge of the flange to provide said interference fit.

10. A prosthetic disc as in claim 1, wherein the peripheral restraining structure comprises:
a groove around a lateral edge of the core; and
a ring structure on at least one of the upper and lower plates, said ring structure having a lip which engages the groove.

11. A prosthetic disc as in claim 10, wherein the lip extends into the groove to form an interference fit between the ring structure and the core.

12. A prosthetic disc as in claim 1, wherein the outer surfaces of the upper and lower plates have at least one surface feature for promoting attachment of the outer surfaces to the vertebrae.

13. A prosthetic disc as in claim 12, wherein the at least one surface feature comprises a plurality of serrations disposed along the outer surfaces.

14. A prosthetic disc as in claim 13, wherein the at least one surface feature further comprises a surface coating.

15. A prosthetic disc as in claim 14, wherein the surface coating comprises plasma sprayed titanium.

16. A prosthetic disc as in claim 13, wherein the at least one surface feature further comprises a plurality of concavities formed by aluminum oxide blasting.

17. A prosthetic disc as in claim 13, wherein the at least one surface feature further comprises at least one fin disposed on each of the outer surfaces.

18. A prosthetic disc as in claim 17, wherein each fin includes at least one hole for further promoting attachment to the vertebrae.

19. A prosthetic disc as in claim 17, wherein each fin is oriented in a straight line in an anterior-posterior direction.

20. A prosthetic disc as in claim 17, wherein each fin is rotated away from an anterior-posterior axis of the disc.

21. A prosthetic disc as in claim 1, wherein the plates comprise at least one metal selected from the group consisting of cobalt chrome molybdenum and titanium.

22. A prosthetic disc as in claim 1, wherein each plate comprises an MRI compatible material coupled with a hardened material forming the inner surface.

23. A prosthetic disc as in claim 22, wherein the MRI-compatible material comprises titanium and the hardened material comprises cobalt chrome molybdenum.

24. A prosthetic disc as in claim 22, wherein the MRI-compatible material comprises titanium and the hardened material titanium nitride.

25. A prosthetic disc as in claim 22, wherein the MRI-compatible material and the hardened material are coupled together using a process selected from the group consisting of lamination, slip fitting, interference fitting and adhesion.

26. A prosthetic device as in claim 1, wherein the core comprises at least one material selected from the group consisting of polymers and ceramics.

27. A prosthetic disc as in claim 1, wherein the mobile core is rigid.

28. A prosthetic disc for insertion between adjacent vertebrae, the prosthetic disc comprising:
upper and lower plates having outer surfaces locatable against the respective vertebrae and inner, curved surfaces, wherein at least one of the upper and lower plates includes a peripheral restraining structure extending about a periphery of the inner surface(s); and
a mobile core disposed between the curved surfaces, the mobile core having bearing surfaces configured to allow the plates to slide and translate over the mobile core when the prosthetic disc is implanted,
wherein the peripheral restraining structure comprises a flange located on at least one of the plates configured to hold the mobile core between the plates, wherein the flange contacts the other plate to limit relative inclination of the plates during sliding movement of the plates over the core, wherein the core includes at least one peripheral protrusion for engaging with the peripheral restraining structure(s) to hold the core captive between the plates during sliding movement of the plates over the core, wherein at least part of the protrusion on the core extends into the flange to provide an interference fit of the core with the flange, and wherein the protrusion comprises a rim around a lateral circumference of the core, the rim having a greater diameter than a diameter of an inner edge of the flange.

29. A prosthetic disc as in claim 28, wherein the inner surfaces of the plates are concave and the core bearing surfaces comprise two convex surfaces for slidably contacting the concave inner surfaces.

30. A prosthetic disc as in claim 29, wherein the concave and convex curved surfaces are spherical.

31. A prosthetic disc as in claim 28, wherein the core comprises a material selected from the group consisting of polymers and ceramics.

32. A prosthetic disc as in claim 28, further including at least one fin extending from each of the outer surfaces of the plates.

33. A prosthetic disc as in claim 32, wherein each fin includes at least one hole for promoting attachment of the fin to vertebral bone.

34. A prosthetic disc as in claim 32, wherein each fin is oriented in a straight line in an anterior-posterior direction.

35. A prosthetic disc as in claim 32, wherein each fin is rotated away from an anterior-posterior axis of the disc.

36. A prosthetic disc as in claim 28, wherein the outer surfaces of the plates are textured to enhance attachment of the plates to the vertebrae.

37. A prosthetic disc as in claim 36, wherein the textured surfaces comprise serrated surfaces.

38. A prosthetic disc as in claim 37, wherein the serrated surfaces further include a plurality of concavities formed by aluminum oxide blasting.

39. A prosthetic disc as in claim 36, wherein the outer surfaces further comprise a surface coating.

40. A prosthetic disc as in claim 39, wherein the surface coating comprises plasma sprayed titanium.

41. A prosthetic disc as in claim 36, wherein the outer surfaces of the plates are flat.

42. A prosthetic disc as in claim 28, wherein each plate comprises an MRI compatible material coupled with a hardened material forming the inner surface.

43. A prosthetic disc as in claim 42, wherein the MRI-compatible material comprises titanium and the hardened material comprises cobalt chrome molybdenum.

44. A prosthetic disc as in claim 42, wherein the MRI-compatible material comprises titanium and the hardened material titanium nitride.

45. A prosthetic disc as in claim 42, wherein the MRI-compatible material and the hardened material are coupled together using a process selected from the group consisting of lamination, slip fitting, interference fitting and adhesion.

46. A prosthetic disc as in claim 28, wherein the mobile core is rigid.

47. A prosthetic disc for insertion between adjacent vertebrae, the prosthetic disc comprising:
    upper and lower plates having outer surfaces locatable against the respective vertebrae and inner, curved surfaces, wherein at least one of the upper and lower plates includes a peripheral restraining structure extending about a periphery of the inner surface(s);
    at least one fin extending from each of the outer surfaces of the plates, wherein each fin includes at least one hole for promoting attachment of the fin to vertebral bone; and
    a mobile core disposed between the curved surfaces, the mobile core having bearing surfaces configured to allow the plates to slide and translate over the mobile core when the prosthetic disc is implanted,
    wherein the peripheral restraining structure comprises a flange of one of the plates configured to hold the mobile core between the plates, wherein the flange contacts the other plate to limit relative inclination of the plates during sliding movement of the plates over the core and wherein the core includes a lateral groove for engaging with the peripheral restraining structure(s) to hold the core captive between the plates during sliding movement of the plates over the core.

48. A prosthetic disc as in claim 47, wherein the flange is adapted to extend into the groove on the core to provide an interference fit of the core with the flange.

49. A prosthetic disc as in claim 48, wherein a portion of the core immediately adjacent the groove has a greater diameter than a diameter of an inner edge of the flange.

50. A prosthetic disc as in claim 47, wherein the inner surfaces of the plates are concave and the core bearing surfaces comprise two convex surfaces for slidably contacting the inner surfaces.

51. A prosthetic disc as in claim 50, wherein the concave and convex curved surfaces are spherical.

52. A prosthetic disc as in claim 47, wherein the core comprises a material selected from the group consisting of polymers and ceramics.

53. A prosthetic disc as in claim 47, wherein the outer surfaces of the plates are textured to enhance attachment of the plates to the vertebrae.

54. A prosthetic disc as in claim 53, wherein the textured surfaces comprise serrated surfaces.

55. A prosthetic disc as in claim 53, wherein the outer surfaces further comprise a surface coating.

56. A prosthetic disc as in claim 55, wherein the surface coating comprises plasma sprayed titanium.

57. A prosthetic disc as in claim 53, wherein the outer surfaces of the plates are flat.

58. A prosthetic disc as in claim 47, wherein the mobile core is rigid.

59. A method for restraining spacing between adjacent vertebrae, the method comprising:
    implanting an upper plate against a lower surface of an upper vertebral body;
    implanting a lower plate against an upper surface of a lower vertebral body; and
    disposing a core between the upper and lower plates, the core comprising at least one peripheral protrusion,
    wherein when the prosthetic disc is implanted, the core floats between spherical cavities in each of the upper and lower plates, the plates restraining peripheral movement of the core using at least one peripheral restraining member that comprises an aperture, and wherein the at least one peripheral protrusion is passed through the aperture to hold the core captive between the plates during sliding movement of the plates over the core.

60. A method as in claim 59, wherein implanting each of the plates comprises sliding a fin on each plate into a corresponding groove formed in its respective vertebral body.

61. A method as in claim 60, wherein sliding the fin is performed in a direction from posterior to anterior.

62. A method as in claim 60, wherein sliding the fin is performed in a lateral direction.

63. A method as in claim 60, wherein sliding the fin is performed in angled direction between posterior-anterior and lateral.

64. A method as in claim 60, wherein implanting further comprises contacting textured outer surfaces of the upper and lower plates with the upper and lower surfaces of the vertebral bodies.

65. A method as in claim 59, wherein the mobile core is rigid.

66. A method for assembling a prosthetic disc for insertion between adjacent vertebrae, the method comprising:
    movably coupling a rigid core with a first endplate to form an interference fit between the core and the first endplate, wherein the core comprises a peripheral protrusion and the first endplate comprises a peripheral restraining structure with an aperture, and wherein the peripheral protrusion is passed through the aperture;
    contacting the core with a second endplate; and
    allowing the core to slide and translate within the peripheral restraining structure when the prosthetic disc is implanted.

67. A method as in claim 66, wherein coupling the core with the first endplate comprises snap fitting the core into the endplate.

68. A method as in claim 66, wherein coupling the core with the first endplate comprises engaging a peripheral protrusion of the core with a peripheral restraining structure of the first endplate.

* * * * *